United States Patent [19]

Mattioli et al.

[11] Patent Number: 4,666,428
[45] Date of Patent: May 19, 1987

[54] SEMI-RIGID PENIAL PROSTHESIS FOR THE TREATMENT OF IMPOTENCE IN THE ERECTION

[76] Inventors: Stefano Mattioli, Via E. Fermi 4, 40033 Casalecchio di Reno, Italy; Hernan M. Carrion, 1150 NW. 14th St., Ste. 600, Miami, Fla. 33136

[21] Appl. No.: 663,858

[22] Filed: Oct. 23, 1984

[51] Int. Cl.4 .............................................. A61F 5/00
[52] U.S. Cl. ..................................................... 128/79
[58] Field of Search .................................. 128/79; 3/1

[56] References Cited

U.S. PATENT DOCUMENTS 4,151,840 5/1979 Barrington ............................ 128/79
4,392,562 7/1983 Burton et al. ......................... 128/79
4,517,967 5/1985 Timm et al. .......................... 128/79

Primary Examiner—Stephen C. Pellegrino
Attorney, Agent, or Firm—Ladas & Parry

[57] ABSTRACT

The prosthesis, to be applied surgically inside one of the cavernous bodies, consists, according to a preferred embodiment, of a series of spheres slightly flattened at the poles and provided with a double row of holes. The spheres are interconnected by a thread which, if tensed by proper devices, causes the stiffening of the prosthesis.

4 Claims, 8 Drawing Figures

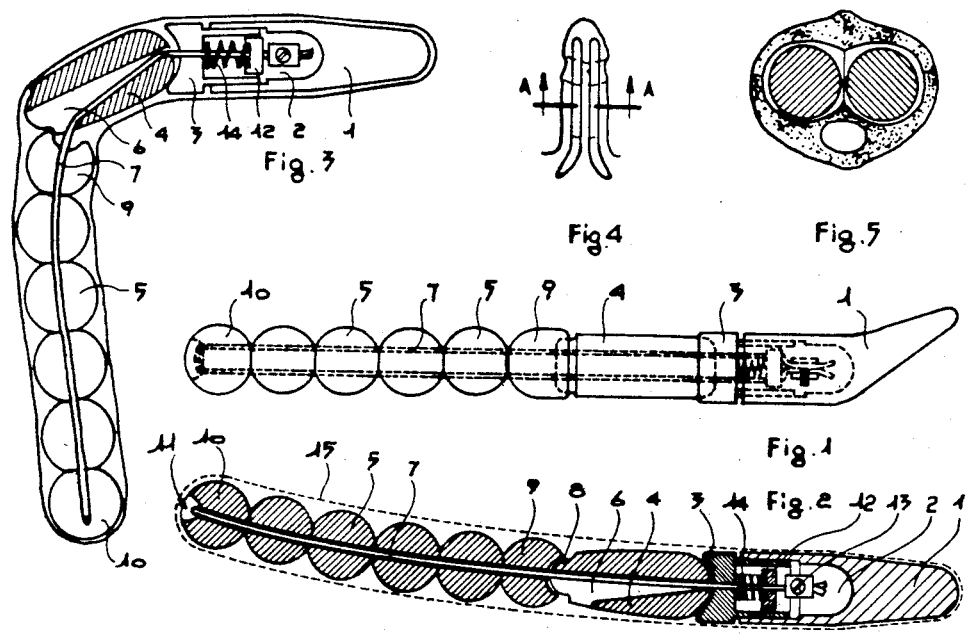
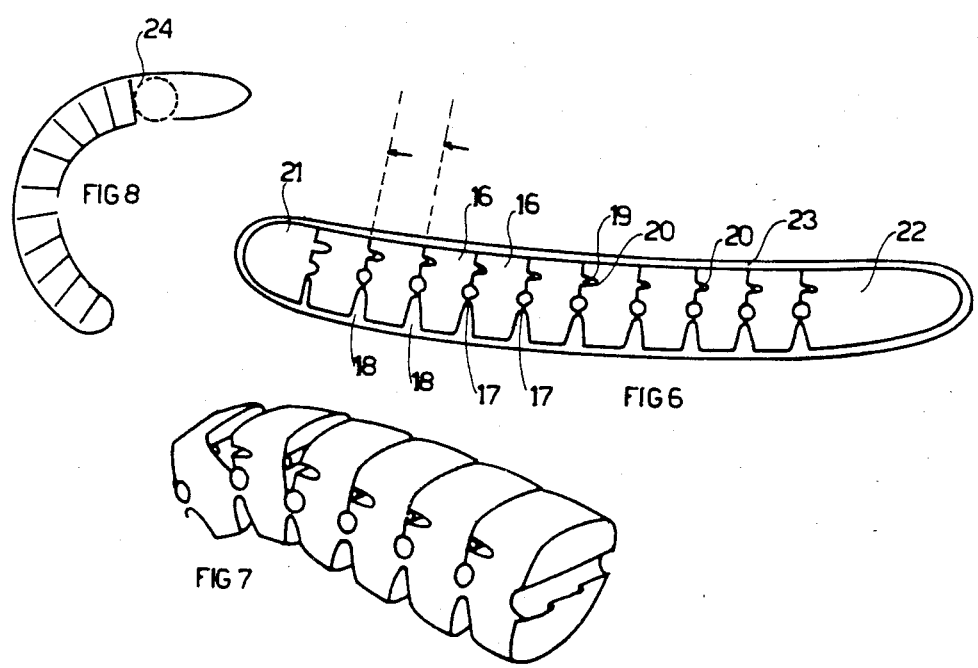

SEMI-RIGID PENIAL PROSTHESIS FOR THE TREATMENT OF IMPOTENCE IN THE ERECTION

The present invention provides for a semi-rigid penial prosthesis for the treatment of those cases of impotence in which, for various reasons, the erection cannot be reached.

There are already known urologic protheses for the same purposes, consisting of rigid or semi-rigid elements that are applied surgically, and have the function of allowing the male organs to reach the erect state.

Some of these prostheses are made of silicone rubber with a core of interlaced silver wires, so as to form malleable but sufficiently rigid elements, to be inserted in the cavernous bodies.

Other prostheses consist of cylinders made of elastomer material, filled with a suitable foam so as to be flexible enough, while still another kind of prostheses comprises inflatable, surgically applicable bodies.

All the prostheses used so far, however, have many inconveniences as they need connexions and devices for inflation, or, though being made of malleable material, are always somewhat rigid, constituting therefore a real physical nuisance.

The need is therefore being felt for a prosthesis that, though reaching a sufficient degree of stiffness when necessary, is also flexible in normal conditions, so as to be hardly felt and to permit to avoid the above mentioned inconveniences.

To this end, the present invention provides for a prosthesis consisting of a series of elements independent from each other in normal conditions, but provided with means for stiffening the prosthesis, when required.

Said means may consist e.g. of a series of spheres slightly flattened at the poles, provided with holes through which passes a thread of proper material. This thread, if tensed by means of devices described later on, keeps the spheres pressed together so as to form a sufficiently rigid unit.

According to another preferred embodiment, the prosthesis according to the invention consists of a series of elements of plastic material, linked to each other by a thin tongue of the same material, so that the whole may be folded, elements which are provided with snap joint elements allowing, when necessary, to set the prosthesis in a semi-rigid position.

The present invention will be now described in detail, by mere way of non limiting example, with special reference to the accompanying drawings, wherein:

FIG. 1 is a view from above of a prosthesis according to the invention;

FIG. 2 is a side view of a prosthesis according to invention in upright position;

FIG. 3 is a side view of the prosthesis according to the invention in resting position;

FIG. 4 is a schematic representation of the way a prosthesis according to the invention is applied;

FIG. 5 shows the section along the line A—A of FIG. 4;

FIG. 6 shows the section of another embodiment of the invention;

FIG. 7 is the partial perspective view of the element of FIG. 6;

FIG. 8 shows schematically a side section of the prosthesis of FIG. 6.

According to a first embodiment the prosthesis according to the invention comprises a support 1 to be applied at the root of the cavernous bodies, provided with a cavity 2 closed by an element 3 which acts as a support for the remaining part of the prosthesis, comprising a base element 4 and a series of spheres or the like 5, 9 and 10.

The element 4 has a cuneiform opening 6, while the spheres are provided with pairs of holes. The spheres are linked among them by a thread 7, passing through said holes. The ends of thread 7 pass then through the cuneiform aperture 6 and from hence, through passages not shown, they reach the inside of cavity 2 through the closure element 3.

The surface of the spheres 5, 9 and 10 is flat at the mutual contact points.

In the end sphere 10 there is a groove 11 or the like, linking the two holes present in the sphere.

As already said, spheres 5, 9 and 10 are linked to a body 4 by means of a thread, the extremities of which end up both inside cavity 2, where, after passing through a head element 12, are blocked by a device 13 or the like.

A helicoidal spring 14 tends to separate the head element 12 from the closure element 3, exerting thus a pulling on thread 7. It should be noted, by the way, that one end of body 4, namely the lower one in FIG. 2, is shorter than the other.

All the above described components are enclosed in a sheath made of silicone elastomer or silicone sponge.

The above prosthesis is inserted, after being subjected to adaptability test by gauging (calibration) by Hegar dilator, in one of the cavernous bodies.

The base 1 will be in the vicinity to the roots, while the semi-rigid part, that is to say the spheres kept by the threads, is inserted in the remaining part of the urethra.

To bring the prosthesis in the rigid state, it is sufficient to exert a slight pulling on the spheres, which makes the spheres/thread unit move forward in contrast to spring 14, until sphere 9 is inserted on the convexity 8 of body 4. Through the head element 12 the spring exerts such a tension on the thread as to keep the flat surfaces of the spheres pressed together, so that the prosthesis is kept in an upright position.

By means of a slight pulling, it is possible then to disengage the sphere 9 from body 4.

In this case, as the lower part of body 4 is shorter, no pulling is exerted on thread 7 anymore; as a consequence, all the components of the prosthesis are independent from one another, allowing thus the prosthesis itself to be completely flexible. Due to the fact that thread 7 is double, instead of single, any side shiftments of the prosthesis are prevented.

At the moment of application, moreover, it is possible to vary the length of the prosthesis according to the various requirements, by simply varying the number of the spheres 5 that are being employed.

In the FIGS. 6 to 8 there is represented another preferred embodiment of the prosthesis according to the invention, which consists of a single piece body comprising a series of elements 16 of plastic material, set one after the other and connected with one another in correspondence of areas 17, having thinner section.

Each of the elements 16 is so shaped, in the lower part, as to define, between two subsequent elements, a cuneiform empty space allowing the whole prosthesis to fold, reaching the shape showed in FIG. 8.

In the upper part of each element 16 there are present a front small tongue 19 and a rear groove 20, fitting together so as to form a joint. The front end portion of the prosthesis is a rounded element 21, while the rear end portion is a support 1 for allowing the application thereof to the root of the cavernous bodies.

The whole is enclosed in a sheath 23, made too of suitable plastic material.

The group of elements 16 is preferably connected with support 22 by means of a hinge joint 24 or the like, schematically illustrated in FIG. 8.

Any expert in the art may provide for several amendments or variations, which should all fall, however, within the ambit of the present invention.

We claim:

1. A semi-rigid penial prosthesis comprising independent elements having complementary contact surfaces, said elements being slightly flattened at their contact ends and having two holes through which passes a thread, one of said elements having a groove therein, a second of said independent element having a concave opening, and a base element with an upper and lower part, the upper part of said base element longer than the lower part, said base element having a convex end and, internally, a cuneiform opening, and a head element, all of said elements connected by a thread passing through said holes and through said opening in the base element, and said thread passing through said head element, a helical spring separating the head element from a closure element, all of said elements enclosed in a sheet made of silicone elastomer.

2. A semi-rigid penial prosthesis as defined in claim 1, wherein said sheath is made of a silicone sponge.

3. Semi-rigid penial prosthesis according to claim 1, comprising a number of elements that may be variously coupled, so that the overall length differs, connected together by a substantially unextensible element, on the inside thereof, said element secured to an elastic means at its end, suitable for exerting on said unextensible connecting element a pulling which tends to keep close together said variously couplable means of which the prosthesis consists.

4. A prosthesis according to claim 1, and providing for a support to be applied at the root of the cavernous bodies; a series of spheres connected with said support by means to an unextensible filiform element, that can move in contrast to elastic means; a central body located between said spheres and said support, said central body being so shaped as to allow the spheres to be shifted from a position in which said thread is kept tensed by said elastic means to a position in which no pulling is exerted on said thread anymore.

* * * * *